United States Patent [19]

Hoffmann et al.

[11] Patent Number: 5,780,688
[45] Date of Patent: Jul. 14, 1998

[54] SUPPORTED-CATALYST AND USE OF SAME

[75] Inventors: Ulrich Hoffmann, Northeim; Ulrich Kunz, Claustihal; Hartmut Bruderreck, Borken; Klaus Gottlieb, Herdecke; Kuno Schadlich, Essen; Stefan Becker, Bochum, all of Germany

[73] Assignee: Veba Oel AG, Gelsenkirchen, Germany

[21] Appl. No.: 407,024

[22] PCT Filed: Oct. 2, 1993

[86] PCT No.: PCT/EP93/02696

§ 371 Date: Apr. 5, 1996

§ 102(e) Date: Apr. 5, 1996

[87] PCT Pub. No.: WO94/08713

PCT Pub. Date: Apr. 28, 1994

[30] Foreign Application Priority Data

Oct. 10, 1992 [DE] Germany ............ 42 34 779.3

[51] Int. Cl.$^6$ ............ C07C 29/04; C07C 2/04; C07C 2/56; C07C 41/00
[52] U.S. Cl. ............ 568/697; 568/896; 568/897; 502/439; 502/108; 502/182; 502/185; 502/313; 502/527; 585/250; 585/510; 585/709; 585/721

[58] Field of Search ............ 502/439, 527, 502/313, 180, 182, 185; 585/520, 510, 250, 709, 721, 400, 446; 521/29; 568/697, 896, 897

[56] References Cited

U.S. PATENT DOCUMENTS

| | | | |
|---|---|---|---|
| 4,426,508 | 1/1984 | Dromard et al. | 528/23 |
| 4,508,845 | 4/1985 | Dromard et al. | 502/159 |
| 4,661,411 | 4/1987 | Martin et al. | 428/421 |
| 4,791,081 | 12/1988 | Childress et al. | 502/62 |
| 5,132,099 | 7/1992 | Hiramatsu | 423/584 |
| 5,233,096 | 8/1993 | Lundquist et al. | 568/727 |
| 5,244,929 | 9/1993 | Gottlieb | 521/29 |

*Primary Examiner*—Wayne Langel
*Assistant Examiner*—Tanaga A. Boozer
*Attorney, Agent, or Firm*—Antonelli, Terry, Stout & Kraus LLP

[57] ABSTRACT

The invention concerns a supported catalyst in the form of packing and constructed on an open-pore support material on whose external and internal surfaces a macro-porous ion exchange resin is mechanically and/or chemically affixed.

40 Claims, 2 Drawing Sheets

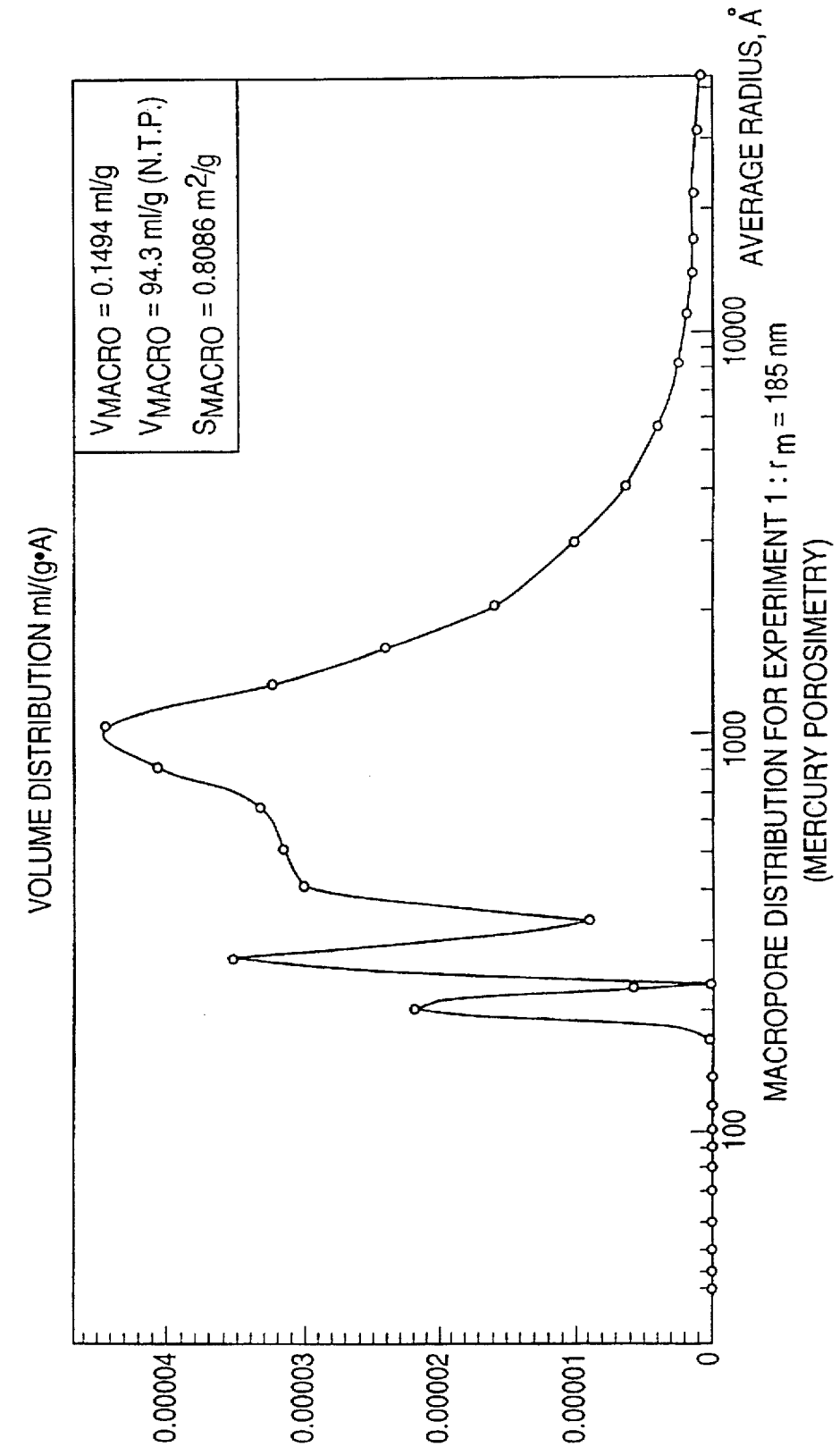

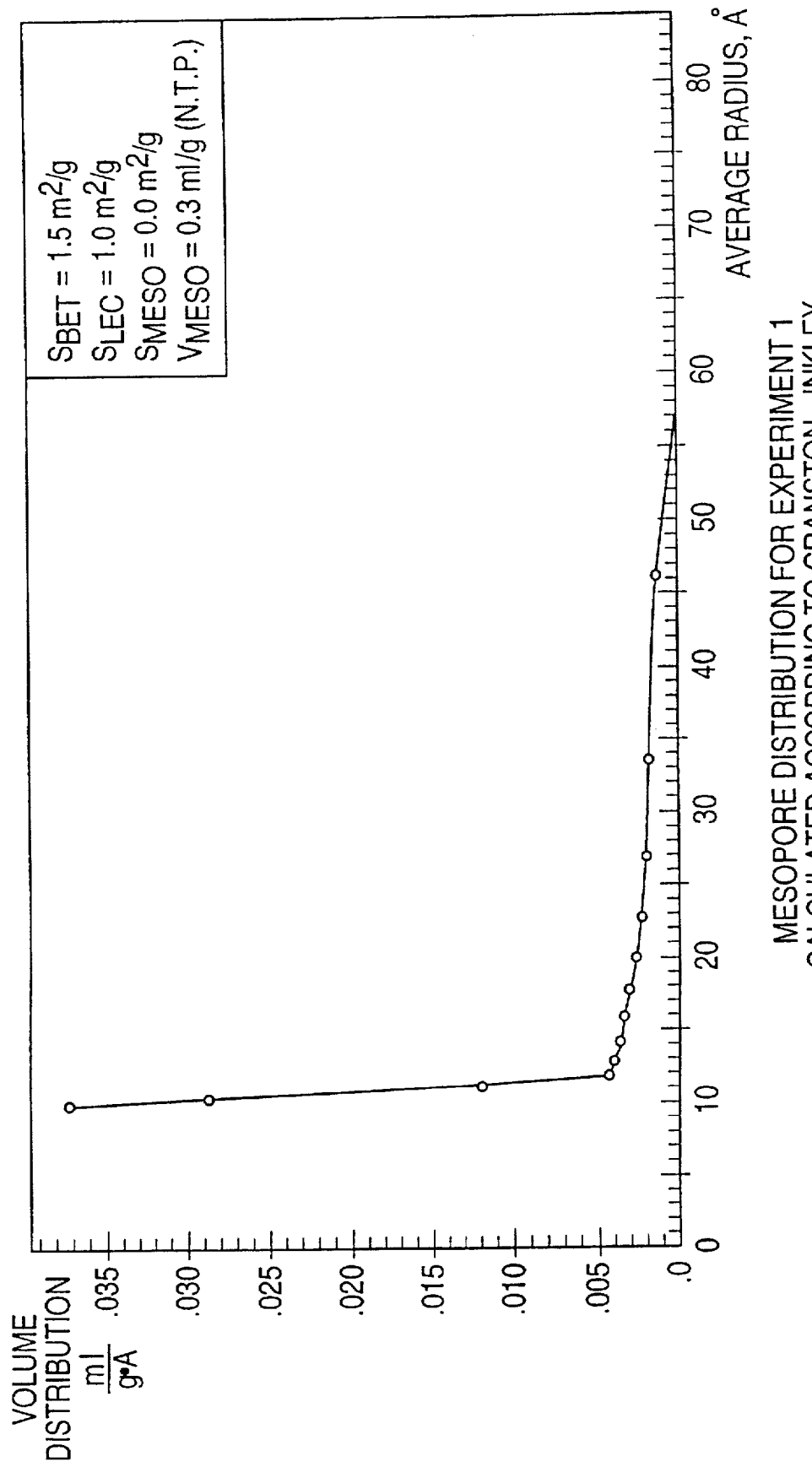

SUPPORTED-CATALYST AND USE OF SAME

The invention concerns a supported catalyst and use of same.

The development of new supported catalyst containing sulphonic acid groups on a polymer frame, is of great importance for a number of industrial chemical processes, for example the production of certain ethers from the reaction of $C_4$ or $C_5$ fractions of the refinery technology with methanol or ethanol as admix components for the production of fuel (cf. Hydrocarbon Processing, November 1990, pp.126, 128).

To produce improved, particularly more environmentally friendly anti-knock petrol qualities, methyl tertiary butylene ether (MTBE) and tertiary amyl methyl ether (TAME) or tertiary butylene ethylether (ETBE) are particularly important admix components.

The processes to produce these components are generally carried out as reaction distillation processes or processes to treat and/or react the products by catalytic distillation.

In case of catalytic distillation the reaction and the processing of the reaction mixture by distillation and/or rectification, which usually takes place in a following step of the process, are carried out in one single reaction apparatus only, which also includes the processing part.

In this connection the introduction and affixing of the catalyst in the reaction apparatus represents a special problem. Usually in the case of solid or supported catalysts a filling of the catalyst into one or several superposed solid beds, permeated by the reaction mixture, is provided.

When the macro-porous cross-linked polystyrene sulphonic acid, used in the industrial production of the MTBE or TAME, is used in spherical form as loose filling in a solid bed as catalyst in the reaction of methanol and butylene, disadvantages like higher resistance to flow, edge flow as well as the wear of the catalyst are involved.

To avoid these disadvantages in a process to carry out chemical reactions in a reaction-distillation apparatus it has been proposed to accommodate the catalyst consisting of macro-porous cross-linked gel pellets of a polystyrene sulphonic acid in closed pouches, which are constructed from and retained by a wire netting and are assigned to a solid bed made to suit the reaction apparatus by coiling in the form of a spiral, cf. EP-A-0 466 954.

It has been further proposed for the purpose of improving the material exchange properties of the solid bed catalyst packing to construct the catalyst in the shape of exchange bodies like Raschig rings, for which purpose a mixture of cross-linked styrene divinyl benzene copolymer in ground form is coextruded with the thermoplastic polypropylene to such an exchange shape and is sulphonated afterwards, cf. FR-A-2 297 083.

This concept has been further developed inasmuch the formed bodies were produced directly from macro-porous ion exchange resins without the use of a thermoplastic material, cf. DE-A-3 930 515. The formed bodies obtained by this method have the expected good material exchange properties as well as a good catalytic activity. It is, however, not easy to manufacture these in production quantities and they leave a lot to be desired regarding their mechanical strength.

From U.S. Pat. No. 4,250,052 supported catalysts are known in the form of a packing, which can be coated with a polymer made of vinyl aromatic monomers and can be subsequently sulphonated. For this purpose the polymer is dissolved, applied to the support and the solvent is then removed again. A disadvantage of this process and/or of the catalyst produced in this manner is that the polymers mentioned cannot be strongly cross-linked as otherwise they could not be dissolved. The result of this is that they can be corroded, separated or dissolved by the reaction mixture also. In addition, in the manner mentioned, no macro-porosity for the polymer can be achieved.

The object of the invention is to produce a supported catalyst with material exchange properties which can be also produced in production quantities.

This objective is achieved by supported catalysts according to the claims 1 to 14 as well as by a process to carry out chemical reactions by using these supported catalysts according to claims 15 to 24.

The supported catalysts according to the invention in the form of packing are constructed from a basic body consisting of open porous support material, on the external and internal surface of which a macro-porous ion exchange resin is affixed mechanically and/or chemically.

A chemical affixing may be preferred and is obtained, for example by silanising the surface of the open-porous support material with subsequent polymerisation build-up.

The packing of the supported catalyst is constructed as Raschig rings, Berl saddles, torus saddles, packing rings with web or cross web, Pall rings, other hollow bodies, hollow spheres, ordered packages, honeycomb bodies and the like with a proportion of the hollow space of the macro-porous ion exchange resin being 5 to 95%.

The support material of the aforementioned supported catalyst consists of open-pore glass, sintered glass, open-pore ceramic material on aluminium silicate base, sintered glass ceramics, foam ceramics, activated carbon or activated coke.

In the case of sintered glass or sintered glass ceramics the surface area can be increased by a prior treatment with aqueous alkali hydroxide solution. By this the number of silanol groups on the surface will be increased on the one hand, which surface is then accessible for silanisation and by the etching process a rougher surface is created on the other, thereby favouring a mechanical affixing on the polymer applied.

While glass with open pores, sintered glass, sintered glass ceramics or ceramic material with open pores are commercially available already in a basic or packing form suitable for material exchange purposes, activated carbon or activated coke with suitable pore sizes can be used according to the invention for catalyst beds. Suitable pore sizes are obtained from bulk material after a selection process from suitable sieved material in selected size ranges.

The macro-porous ion exchange resin on and in the support material is preferably a macro-porous cross-linked polystyrene sulphonic acid, whereby a different degree of cross-linking can be accomplished to correspond with the requirements by using greater or lesser amounts of divinyl, benzene or diisopropenyl benzene. The polymer is preferably cross-linked to such a high degree, that it cannot be dissolved by the reaction mixture of the reaction to be catalysed.

The ion exchange resin can be applied to the support material by two different processes.

In case of the so called impregnating polymerising process the formed bodies are impregnated with the reaction mixture, the excess impregnating solution is removed and subsequently the polymerisation is carried out.

In case of the precipitating polymerising process the packing is in excess in the reaction mixture during the polymerisation. The advantages of the precipitation polymerising process are a very uniform distribution of the polymer in the pores of the support material, in addition a high porosity, since the solvent can act as a pore former, as well as the simple production manner, since no steps are required to even out the distribution of the monomers on the support.

An additional advantage is that the polymer content in the completed ion exchange resin can be set simply by the ratio of a suitable solvent to the monomer mixture and that the polymer, when using the appropriate solvent, is already in the swollen form so that possible damage of the support material by the swelling process can be avoided to a great extent. Methanol or i-octane, as well as pentadecane may be used as solvents. A $C_{14}$- to $C_{17}$-n-paraffin fraction can also be used.

By the process mentioned a macro-porous polymer is produced in the pores and on the surface of porous packing, which will subsequently receive ion exchange properties by sulphonation.

In case of the precipitating polymerisation process the polymerisation is carried out depending on the concentration of the original materials styrene and divinyl benzene or disopropyl benzene in the pore former or of the solvent in the pores of the packing up to that degree of polymerisation, at which the formed polymer in flaky form becomes insoluble in the pore former and/or the solvent and precipitates. The polymer flakes produced in this manner in the pores of the support material can be affixed in the pores of the support material purely mechanically and are protected from mechanical damages by the surrounding support material.

For certain reactions it is useful to treat supported catalysts of the type described above with Group7 or Group 8 metals of the periodic table, particularly with palladium, platinum, ruthenium or rhodium in quantities of 0.1 to 100 g/kg of the ion exchange resin.

As has already been indicated, the polymer can be additionally affixed chemically on the support material. A suitable chemical coupler is used for this purpose. For example silanes are suitable couplers for all formed bodies which have OH groups on their surfaces.

If the polymer to be coupled has a vinylic monomer base, vinyl-group carrying silanes are preferred as couplers, particularly phenyl-vinyl diethoxysilane, phenyl-methyl vinyl silane, triethoxy-vinyl silane or trichlor-vinyl silane.

The supported catalyst can be produced by impregnating the packing with 0.1 to 60% by weight with a mixture consisting of 10 to 80, preferably 30 to 70% by weight of styrene, 2 to 25, preferably 5 to 10% by weight of divinyl benzene, 1 to 88, preferably 20 to 50% by weight of a pore former or of a solvent as well as an effective quantity of a polymerisation initiator; carrying out the polymerisation reaction under a temperature increase of 30° to 90° C.; and subsequently treating the polymer material affixed in the pores of the packing with a sulphonating acid. In this case the proportion by weight of the pore former or of the solvent is selected so that the proportion by weight of the mixture of styrene and divinyl benzene adds up to 100% by weight.

A supported catalyst produced according to the precipitating polymerisation process can be obtained by adding a mixture of 10 to 80, preferably 20 to 50% by weight of styrene, 2 to 25, preferably 5 to 10% by weight of divinyl benzene, 1 to 88, preferably 20 to 50% by weight of a pore former or solvent as well as an effective quantity of a polymerisation initiator on the one hand and a $C_{14}$- to $C_{17}$-n-paraffin fraction on the other in a weight ratio of 10 to 1 to 1 to 10, to 5 to 50% by weight of the support material, based on the total mixture, conditioning it under vacuum, polymerising, washing out the excess pore former and externally adhering polymer gel, followed by sulphonating.

As pore formers $C_6$- to $C_{16}$-alkanes, e.g. n-heptane, pentadecane, i-octane as well as $C_9$- to $C_{13}$-fractions of the n-paraffin production can be used. These pore formers have good solubility for the styrene and divinyl benzene monomers used for the production of the ion exchange resin, but only a slight swelling ability for the polymer produced (cf. Catalytic Chemistry, Bruce C. Gates, John Wiley & Sons, 1992, p.221).

In this manner a solid phase, consisting preferably of microspheres, is formed in the hollow spaces of the support and on the support material, and the volume originally occupied by the solvent for the monomers remains as macro-pores after the removal of the solvent, which pass through the entire cross-linked polystyrene and thus enable a good access of the reacting materials for the intended chemical reactions after sulphonation. At the same time an increase of the active surface can be achieved by this.

This is why in a preferred embodiment the pore formers can be also solvents for the monomer mixture in case of the precipitation polymerisation. In case of the precipitation polymerisation lower alkanols like methanol are also suitable as solvent. Combinations of solvent and pore former can also be used.

The sulphonating acid may be an aromatic or an aliphatic sulphonic acid, chlorosulphonic acid or sulphuric acid. Furthermore, sulphur dioxide as well as sulphur dioxide addition compounds like that of dioxane, dimethyl aniline or pyridine are suitable.

Sulphuric acid is less preferable, as the concentration necessary or adequate sulphonation has a noticeable oxidizing affect and may lead to the disintegration of the polymer frame.

Preferred aromatic sulphonic acids are benzene sulphonic acids and preferred aliphatic sulphonic acids are methyl sulphonic acids.

In a further preferred embodiment the acids may also contain solvents like chloroform, nitromethane or acetonitrile.

The supported catalysts according to the invention are generally used to carry out the chemical reactions of etherification, esterification, hydrogenation, alkylisation, hydration, dimerisation, oligomerisation or combination of these as well as the respective reverse reactions.

Particularly preferred is the carrying out of one of the above mentioned chemical reactions with simultaneously applied separating operation like adsorption, absorption, extraction, stripping, distillation, rectification, fractionating, membrane process or the like to separate the required products. In this case the counter-current of the gaseous or liquid phase is suitable for a single or multiple phase gaseous and liquid reaction, since the supported catalysts according to the invention have a high degree of spacing and thus cause a low pressure loss.

A preferred chemical reaction for using the supported catalyst according to the invention is the chemical reaction of etherification and the separation of the reaction products by reactive distillation to obtain tertiary alkyl ethers from the reaction of alkanoles with alkenes; such as to obtain MTBE from the reaction of methanol with i-butylene; to obtain i-propyl-tertiary butylether (PTBE) from the reaction of i-propanol with i-butylene; to obtain ETBE from the reaction of i-butylene with ethanol; or to obtain TAME from the reaction of i-pentene-(1) or i-pentene-(2) with methanol. Further preferred reactions are the production of i-propanol from the reaction of propylene with water and the production of tertiary butyl alcohol (TBA) by reacting i-butylene with water.

This present invention is explained in detail based on the following examples as well as the results contained in Tables 1 and 2 and the FIGS. 1 and 2.

EXAMPLE 1

As support material formed bodies made of open-porous sintered glass in the form of Raschig rings with the dimensions 8.8 mm:9 mm (outside diameter×height).

This support material is characterised by a surface of up to 0.4 m$^2$/g and a pore volume of up to 70%. The pore diameter can be varied from 1.6 μm to 400 μm, the temperature resistance is up to 450° C.

40 pieces of the aforementioned rings have a mass of 12.5 g and were impregnated with a mixture of 22.7 g styrene, 13.7 g pentadecane, 2.9 g divinyl benzene and 50 mg azoisobutyronitrile. The impregnation solution not accommodated in the pores was removed. The impregnated rings were placed into a sealed, pressurised metal container and were polymerised at a temperature of approx. 75° C. in a heating cabinet for the period of 10 h. The pressurized container is necessary to prevent the changing of the monomer mixture during the polymerisation by vapourisation processes. The polymer content of the rings treated in this manner was approx. 20 to 25% by weight. The rings were cooled afterwards to room temperature and subjected to sulphonation. 500 mL of the formed bodies obtained were covered completely with chloroform and made to react with 50 mL of chlorosulphonic acid for 20 h while excluding moisture. Subsequently the reaction solution was poured slowly on ice, the formed bodies were rinsed with chloroform and rinsed with methanol and deionised water to completely remove the sulphonating agent and acid. The formed bodies were stored in water.

EXAMPLE 2

12.5 g of the support material described in Example 1 was added to a mixture with the weight ratio of 1 to 1 of 22.7 g styrene, 2.9 g divinyl benzene, 13.8 g i-octane, 0.05 g azoisobutyronitrile on the one hand and $C_{14}$- to $C_{17}$-n-paraffin fraction on the other, so that the formed bodies to be impregnated were fully covered. Afterwards the mixture was conditioned for 2 min under vacuum to fill all the pores. The mixture was subsequently heated for 16 h at 60° C.

The polymer gel surrounding the formed bodies as well as the pore former were washed out after the completion of the reaction with chloroform. The formed bodies produced thus contained approx. 10% by weight polymer.

By repeating the treatment according to this method the polymer content can be increased to approx. 20% by weight.

500 mL of the formed bodies obtained were fully covered with chloroform and made to react with 50 mL chlorosulphonic acid for 20 h while excluding moisture. Subsequently the reaction solution was poured slowly on ice, the formed bodies were rinsed with chloroform and rinsed with methanol and deionised water to completely remove the sulphonating agent and acid. The formed bodies were stored in water.

The abbreviations used in Table 1 have the following meanings:

Cap: Capacity of the catalyst used $n_i$: Hole flow of the component i

T: Dwell time $X_i$: Conversion of the component i $Y_i$: Yield of MTBE based on the component i Component i: MeOH or IB MeOH: Methanol IB: i-butylene sSDCmT: Sulphonated styrene/divinyl-benzene copolymer, macro-porous, produced by impregnating polymerisation sSDCmF: Sulphonated styrene/divinyl-benzene copolymer, macro-porous, produced by precipitating polymerisation sSDC: Sulphonated styrene/divinyl copolymer MPI: Macro-porous ion exchange rings Table 2 shows the effective reaction speeds of the MTBE formation. They are based on the capacity of the catalyst on the one hand, on the mass on the other, and finally on the bulk volume of the dry catalyst.

The bulk density of the dry catalyst was established by weighing the mass which takes up a given bulk volume, or by measuring the volume of a given mass. In the present case a volume has been assumed.

TABLE 1

Experimental settings of the catalysts used
The pressure and temperature have been held constant in all experiments (p = 20 × 10$^5$ Pa; T = 65° C.)

| Experiment | Catalyst | Cap (meq/g) | Weight (mg) | $n_{MeOH}$ (mmol/min) | $n_{IB}$ (mmol/min.) |
|---|---|---|---|---|---|
| 1 | sSDCmT | 0.506 | 1886 | 30 | 28.57 |
| 2 | sSDC | 0.419 | 1804 | 30 | 28.57 |
| 3 | MPI | 4.63 | 1500 | 30 | 28.57 |
| 4 | A15 | 4.75 | 1928 | 30 | 28.57 |
| 5 | SPC118 | 4.40 | 1932 | 30 | 28.57 |
| 6 | sSDCmF | 0.595 | 2011 | 30 | 28.57 |

| Experiment | Catalyst | t(min) | Conversion X (%) $X_{MeOH}$ | $X_{IB}$ | Yield Y (%) $Y_{MeOH}$ | $Y_{IB}$ |
|---|---|---|---|---|---|---|
| 1 | sSDCmT | 25.18 | 2.7 | 2.8 | 2.7 | 2.8 |
| 2 | sSDC | 25.18 | 0.33 | 0.35 | 0.33 | 0.35 |
| 3 | MPI | 25.18 | 1.85 | 1.95 | 1.86 | 1.96 |
| 4 | A15 | 25.18 | 7.00 | 7.3 | 7.0 | 7.3 |
| 5 | SPC118 | 25.18 | 7.5 | 7.9 | 7.5 | 7.9 |
| 6 | sSDCmF | 25.18 | 0.54 | 0.57 | 0.51 | 0.57 |

TABLE 2

Results of the Catalysts used

| Experiment | Catalyst | P [g/mL] | Rate $e_{eff}$ (MTBE) [mmol/(s eq)] | Rate $m_{eff}$ (MTBE) [mmol/(s g)] × 10$^3$ | Rate $V_{eff}$ (MTBE) [mmol/(s mL)] × 10$^3$ |
|---|---|---|---|---|---|
| 1 | sSDCmT | 0.328 | 14.1 | 7.13 | 2.34 |
| 2 | sSDC | 0.328 | 2.24 | 0.94 | 0.31 |
| 3 | MPI | 0.384 | 1.34 | 6.20 | 2.38 |

TABLE 2-continued

Results of the Catalysts used

| Experiment | Catalyst | P [g/mL] | Rate $e_{eff}$ (MTBE) [mmol/(s eq)] | Rate $m_{eff}$ (MTBE) [mmol/(s g)] × $10^3$ | Rate $V_{eff}$ (MTBE) [mmol/(s mL)] × $10^3$ |
|---|---|---|---|---|---|
| 4 | A15 | 0.577 | 3.82 | 18.14 | 10.46 |
| 5 | SPC118 | 0.506 | 4.43 | 19.49 | 9.86 |
| 6 | sSDCmF | 0.328 | 2.27 | 1.35 | 0.44 |

Rate $Z_{eff}$, MTBE: Reaction speed or the MTBE formation
if Z = e: Based on the equivalent of the resin used
if Z = m: Based on the mass of the resin used
if Z = V: Base on the bulk volume of the resin used The catalyst of Experiment 1 was produced according to Example 1.

The catalyst of Experiment 2 was produced in an analogous manner, but without pore former and thus is not macro-porous. This catalyst is obviously poorer in the test reaction of the MTBE formation than that of Experiment 1.

The catalyst of experiment 6 was produced according to Example 2. Although as far as activity is concerned it is situated below that of the catalyst of Experiment 1, its production, however, is less costly. Experiments 3 to 5 are comparison experiments with standard ion exchangers. A15 is an amberlite of the company Rohm & Haas and SPC118 a product of the Bayer company. The polymer rings with the designation of MPI are described in EP 0 417 407 A1.

The following FIGS. 1 and 2 of the drawing show the macro- and meso-pore distribution of the catalyst according to Experiment 1.

The abbreviations stand for:

in FIG. 1:

$V_{Macro}$=Volume of the macropores in mL/g measured by mercury porosimetry $V_{Macro}$=Volume of the adsorbed helium in the macropores in mL/g (N.T.P.) measured by helium adsorption $S_{Macro}$=Surface of the macropores in m²/g $r_M$=Average pore radius (in this case that of the macropore)

in FIG. 2:

$S_{BET}$=Specific surface of the specimen in m²/g measured according to the BET method $S_{Lec}$=Surface based on the standard isotherms according to Lecloux $S_{Meso}$=Surface of the mesopores in M²/g $V_{Meso}$=Volume of the mesopores According to IUPAC (1972) the diameters are for:

micropores<2 nm mesopores 2 nm to 50 nm macropores>50 nm.

We claim:

1. Supported catalyst having a shape of a packing, and comprising an open porous support material having external and internal surfaces, said external and internal surfaces having affixed thereto a macro-porous ion exchange resin, produced by impregnating or completely covering the support material with a mixture of (a) polymerizable monomers for forming the ion exchange resin and (b) at least one of a solvent therefor and a material for forming pores in the ion exchange resin, and carrying out polymerization.

2. Supported catalyst according to claim 1, produced by a process including an additional step, after said carrying out polymerization, of introducing ion exchange active groups to polymer product of said polymerization.

3. Supported catalyst according to claim 2, obtained by impregnating the support material with 0.1 to 60% by weight of a mixture consisting of 10 to 80% by weight of styrene, 2 to 25% by weight of divinyl benzene, 1 to 88% by weight of at least one of the material for forming pores in the ion exchange resin and the solvent and an effective quantity of a polymerization initiator to initiate polymerization; carrying out the polymerization reaction under a temperature increase of 30° to 90° C.; and subsequently sulphonating.

4. Supported catalyst according to claim 3, wherein the mixture impregnating the support material consists of 30–70% by weight styrene, 5–10% by weight divinyl benzene, 20–50% by weight of at least one of the material for forming pores in the ion exchange resin and the solvent, and the effective quantity of the polymerization initiator.

5. Supported catalyst according to claim 2, obtained by adding a mixture of (A) 10 to 80% by weight of styrene, 2 to 25%, by weight of divinyl benzene, 1 to 88% by weight of at least one of the material for forming pores in the ion exchange resin and the solvent, and an effective quantity of a polymerization initiator to initiate polymerization, and (B) a $C_{14}$- to $C_{17}$-n-paraffin fraction in a weight ratio of (A):(B) of 10:1 to 1:10, to 5 to 50% by weight of the support material, based on the total mixture, conditioning under vacuum, polymerizing, washing and subsequently sulphonating.

6. Supported catalyst according to claim 5, wherein component (A) of the added mixture contains 20–50% by weight styrene, 5–10% by weight divinyl benzene, 20–50% by weight of said at least one of the material for forming pores in the ion exchange resin and the solvent, and the effective quantity of the polymerization initiator.

7. Supported catalyst according to claim 3 or 5, wherein the mixture polymerized to form the ion exchange resin further comprises a fluoro-styrene, a total amount of the styrene and fluoro-styrene being up to 80% by weight.

8. Supported catalyst according to any one of claims 3, 5, 1 and 2, wherein the material for forming pores in the ion exchange resin is a $C_6$ to $C_{16}$ alkane.

9. Supported catalyst according to any one of claims 3, 5, 1 and 2, wherein the material for forming pores in the ion exchange resin is selected from the group consisting of n-heptane, pentadecane, i-octane and a mostly $C_9$ to $C_{13}$ containing n-paraffin fraction.

10. Supported catalyst according to claim 5, wherein said washing washes out exposed polymer gel formed during the polymerization and washes out excess material for forming pores in the ion exchange resin.

11. Supported catalyst according to claim 2 wherein the ion exchange active groups are introduced by means of exposing the resin to a sulphonating acid.

12. Supported catalyst according to claim 11, wherein said sulphonating acid is selected from the group consisting of aromatic and aliphatic sulphonic acids and sulphuric acid.

13. Supported catalyst according to claim 12, wherein the aromatic sulphonic acid is a benzene sulphonic acid.

14. Supported catalyst according to claim 12, wherein the aliphatic sulphonic acid is a methyl sulphonic acid.

15. Supported catalyst according to claim 11, wherein the sulphonating acid is chlorosulphonic acid.

16. Supported catalyst according to claim 2, wherein the polymerizable monomers include vinyl monomers with silane groups, and the catalyst is obtained by reacting material of surfaces of the support material, having OH groups, with the silane groups as a coupler with surface acidic ion exchange groups being affixed by subsequent sulphonation to introduce the ion exchange active groups.

17. Supported catalyst according to claim 1 or 2, wherein the support material is of sintered glass or sintered glass ceramics, which has been contacted with aqueous alkali hydroxide solution prior to impregnating or completely covering the support material with the mixture of polymerizable monomers for forming the ion exchange resin.

18. Supported catalyst according to claim 1 or 2, wherein the ion exchange resin is cross-linked to a sufficient degree so that it cannot be dissolved in a reaction mixture of a reaction to be catalyzed by the supported catalyst.

19. Supported catalyst according to claim 1, wherein the packing is constructed as Raschig rings, Berl saddles, torus saddles, packing rings with web or cross web, Pall rings, hollow spheres, other hollow bodies, ordered packages, or honeycomb bodies, with a proportion of the hollow space of the macro-porous ion exchange resin being 5 to 95 volume %.

20. Supported catalyst according to claim 1 or 19, treated with Group 7 or Group 8 metals of the periodic table, in quantities of 0.1 to 100 g/kg of the ion exchange resin.

21. Supported catalyst according to claim 20, wherein said Group 7 or Group 8 metals is selected from the group consisting of palladium, platinum, ruthenium and rhodium.

22. Supported catalyst according to claim 1 or 19, wherein the support material consists of open-pore glass, sintered glass, open-pore ceramic material on aluminium silicate base, sintered glass ceramics, foam ceramics, activated carbon or activated coke.

23. Supported catalyst according to claim 1 or 19, wherein the macro-porous ion exchange resin is a macro-porous cross-linked polystyrene sulphonic acid.

24. Supported catalyst according to claim 1, wherein said macro-porous ion exchange resin is affixed chemically to said support material.

25. Supported catalyst according to claim 24, wherein the chemical affixing is an affixing achieved by silanising said external and internal surfaces of the support material, to form silanized surfaces, and building up the macro-porous ion exchange resin on the silanized surfaces.

26. Supported catalyst according to claim 1 wherein the solvent is methanol, i-octane, pentadecane or a $C_{14}$- to $C_{17}$-n-paraffin fraction.

27. Supported catalyst according to claim 1, wherein said macro-porous ion exchange resin is affixed mechanically to said support material.

28. Supported catalyst according to claim 1, wherein the support material is a material different from the ion exchange resin.

29. Process for carrying out a chemical reaction, comprising introducing chemical reactants into the presence of the supported catalyst according to claim 1 or 2 and carrying out the chemical reaction, the chemical reaction being at least one selected from the group consisting of etherification, esterification, hydrogenation, dimerization, hydration, alkylization and oligomerization.

30. Process according to claim 29, wherein, simultaneously with the chemical reaction, a separation operation is performed.

31. Process according to claim 30, wherein the separation operation is selected from the group consisting of adsorption, absorption, extraction, stripping, distillation, rectification, fractionating and membrane separation.

32. Process according to claim 29, wherein the chemical reactants and products of the chemical reaction include liquid and gas phases, and wherein the liquid and gas phases flow in opposite directions to each other.

33. Process according to claim 29, wherein the ion exchange resin is sufficiently cross-linked such that the ion exchange resin does not dissolve in the chemical reactants or products of the chemical reaction.

34. Process according to claim 29, wherein the reaction is of alkanols to tertiary alkyl ethers.

35. Process according to claim 29, wherein the reaction is of methanol and i-butylene to methyl tertiary butyl ether (MTBE).

36. Process according to claim 29, wherein the reaction is of i-propanol and i-butylene to i-propyl tertiary butyl ether (PBTE).

37. Process according to claim 29, wherein the reaction is of i-butylene and ethanol to ethyl tertiary butyl ether (ETBE).

38. Process according to claim 29 wherein the reaction is of i-pentene-(1) or i-pentene-(2) with methanol to tertiary axyl methyl ether (TAME).

39. Process according to claim 29, wherein the reaction is of propene and water to i-propanol.

40. Process according to claim 29, wherein the reaction is of i-butylene and water to tertiary butyl alcohol (TBA).

* * * * *